United States Patent [19]
Kelleher et al.

[11] Patent Number: 6,112,123
[45] Date of Patent: Aug. 29, 2000

[54] DEVICE AND METHOD FOR ABLATION OF TISSUE

[75] Inventors: Brian S. Kelleher; Corbett Stone, both of San Diego; Michael Jones, Capistrano Beach, all of Calif.

[73] Assignee: Endonetics, Inc., San Diego, Calif.

[21] Appl. No.: 09/123,509

[22] Filed: Jul. 28, 1998

[51] Int. Cl.[7] .................................................. A61F 7/12
[52] U.S. Cl. ........................... 607/98; 607/101; 607/102; 606/41; 606/27
[58] Field of Search ..................... 607/98, 90, 101–102, 607/104–105; 606/41, 42, 27–31; 600/549

[56] References Cited

U.S. PATENT DOCUMENTS

| | | | |
|---|---|---|---|
| 5,100,388 | 3/1992 | Behl et al. | |
| 5,304,214 | 4/1994 | DeFord et al. | |
| 5,431,649 | 7/1995 | Mulier et al. | |
| 5,575,788 | 11/1996 | Baker et al. | |
| 5,575,811 | 11/1996 | Reid et al. | 607/101 |
| 5,800,432 | 9/1998 | Swanson | 606/49 |
| 5,830,209 | 11/1998 | Savage et al. | 606/15 |
| 5,833,603 | 11/1998 | Kovacs et al. | 600/317 |
| 5,840,031 | 11/1998 | Crowley | 600/440 |
| 5,902,272 | 5/1999 | Eggers et al. | 604/114 |

*Primary Examiner*—Linda C. M. Dvorak
*Assistant Examiner*—Roy Gibson
*Attorney, Agent, or Firm*—Nydegger & Associates

[57] ABSTRACT

A device and method for performing electrolyte assisted tissue ablation of metaplasia in the esophagus includes a shaft with an expandable barrier which is deployable from the shaft's distal end. Also included in the device are an electrode and a temperature/impedance sensor which are each mounted on the shaft. Alternatively, the shaft may be a catheter formed with several lumens which are used independently for housing optical elements and for transferring fluid. In the operation of the device, the distal end of the shaft or catheter is placed in the esophagus proximal the cardia. The barrier is then deployed to the cardia and expanded to seal the esophagus from the stomach. The esophageal volume between the barrier and the catheter is partially flooded with a conducting medium and an electrode is deployed into the conducting medium. The sensor is also deployed into contact with the tissue to be ablated. Using open-loop control, or using temperature, impedance, or visual monitoring for closed-loop control, the metaplasia is ablated by passing radio frequency energy from the electrode and through the conducting medium for contact with the tissue being ablated.

22 Claims, 6 Drawing Sheets

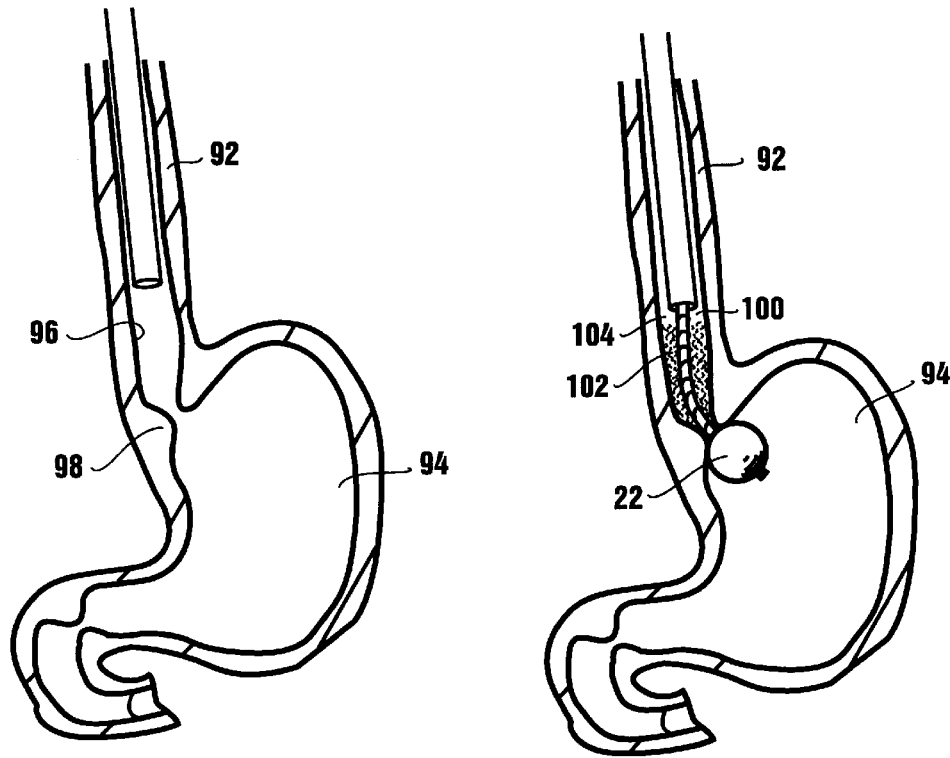
Figure 6A
Figure 6B
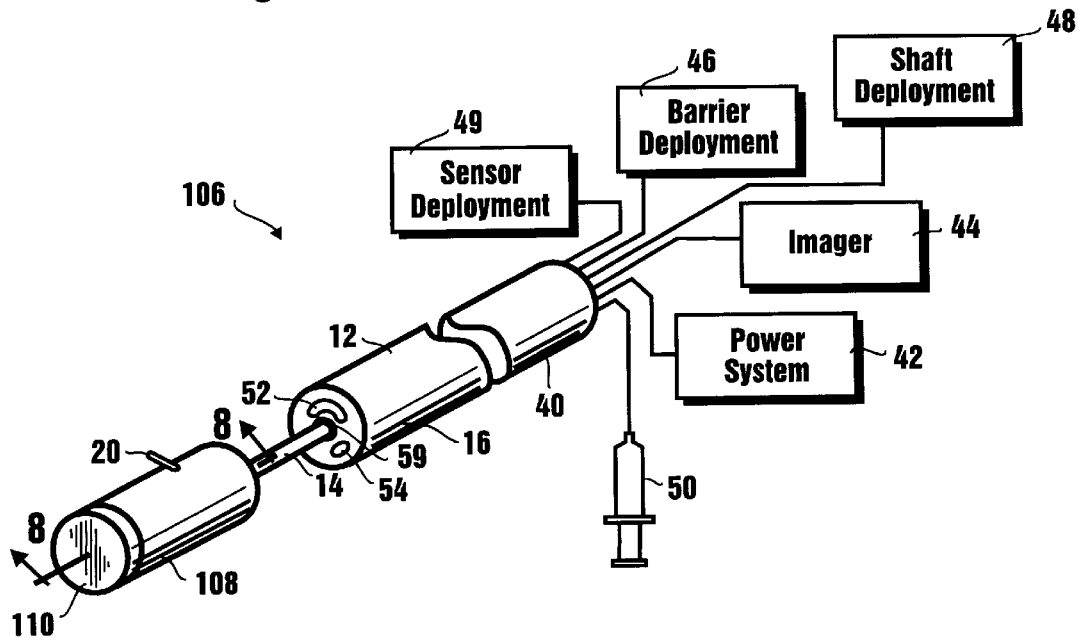
Figure 7

DEVICE AND METHOD FOR ABLATION OF TISSUE

FIELD OF THE INVENTION

The present invention pertains generally to therapeutic medical devices and their methods of use. More particularly, the present invention pertains to devices which are useful for ablating the superficially exposed tissue that defines or establishes a body cavity. The present invention is particularly, but not exclusively, useful for ablating tissue in the lower esophagus.

BACKGROUND OF THE INVENTION

It has been estimated that more than thirteen million Americans suffer from gastroesophageal reflux disease, wherein gastric contents, such as stomach acid, are refluxed into the esophagus. This disease, commonly referred to as GERD, is often associated with an inflammation of the esophagus, known as esophagitis, and can eventually develop into more serious complications known as "Barrett's Esophagus." This development occurs in about ten percent of GERD patients and involves an alteration of the mucosal tissue in the lower esophagus. This alteration involves a transformation from a normal squamous epithelial structure to a columnar form sometimes referred to as specialized intestinal metaplasia, or Barrett's Metaplasia. Further, approximately five percent of Barrett's Esophagus cases subsequently advance to a form of esophageal cancer known as adenocarcinoma. Adenocarcinoma is fatal in about ninety percent of cases.

Various surgical techniques are available to reduce the incidence of reflux, but such procedures are often associated with significant complications. In addition, a number of pharmacological agents, such as protein pump inhibitors (PPI's) are available to reduce the acidity of gastric reflux. Studies have shown that anti-reflux surgery, or treatment with PPI's, can result in a regression of the surface area of Barrett's Metaplasia. However, the only known treatment to completely eliminate the Barrett's Metaplasia is to remove the entire thickness of the afflicted esophageal mucosa. It has been found that following removal of the mucosa, such as by ablation of the tissue, there is a high likelihood that there will be a regrowth of normal epithelial tissue. One way to remove the mucosa is to ablate the tissue by applying various forms of energy to the afflicted tissue. Many presently used ablation techniques, however, have shortcomings.

When tissue ablation techniques are used on tissue in difficult-to-reach locations, such as the lower esophagus, there are at least two significant problems. The first of these involves the difficulty in controlling the depth of the ablation into the tissue. The second involves the difficulty in obtaining uniform ablation over the entire surface area that needs to be ablated. Stated differently, without proper control over how and where the ablation will occur, the result can be "patchy." For example, surgical procedures involving cauterization, laser photoablation, photodynamic therapy, and argon plasma coagulation, all employ well known techniques which require probing the body cavity with an ablating apparatus and then moving the apparatus over the surface area to be ablated. The problem, however, is that surface irregularities, folds into the tissue, and variations in the anatomical configurations of body cavities make each of these techniques somewhat problematical in the uniformity of their ablation. As a result, only a portion of the tissue to be ablated may be destroyed, and in some areas, more tissue may be ablated than was intended. In the case of ablation of Barrett's Metaplasia, by not ablating all of the metaplastic tissue, normal epithelium that regrows over adjacent ablated regions may grow over the unablated region making it difficult to detect an early stage adenocarcinoma.

A technique which has promise in overcoming the shortcomings of the techniques mentioned above is "electrolyte assisted" ablation This form of ablation relies on contacting the tissue to be ablated with an electrolyte, such as a fluid or gel. Electrical energy is applied through the electrolyte to the tissue in contact with the electrolyte. Because the electrical resistance of the electrolyte-tissue interface is significantly high relative to the resistance of the electrolyte itself, most of the energy will be dissipated at this interface in the form of heat, leading to thermal ablation of the superficial tissue at this interface. With electrolyte assisted ablation, the "patchy" problem mentioned above is no longer a concern, since an electrolyte in the form of a liquid or gel will effectively bathe the entire surface area of the tissue that is to be ablated.

Several examples of electrolyte assisted ablation can be given. In each case, however, it should be noted that the device which is used to accomplish the ablation is intended to accommodate a particular anatomy.

U.S. Pat. No. 5,100,388, which issued to Behl et al. for an invention entitled "Method and Device for Thermal Ablation of Hollow Body Organs," discloses a catheter having a conductive material delivery lumen and a distal tip heating element which is suited for hollow body organs, such as the gallbladder. For another type of body cavity, U.S. Pat. No. 5,304,214, which issued to DeFord et al. for a "Transurethral Ablation Catheter," discloses a device that is specifically intended to selectively ablate prostatic tissue about the prostatic urethra. For another, entirely different purpose, U.S. Pat. No. 5,431,649, which issued to Mulier et al. for a "Method and Apparatus for R-F Ablation," discloses a method and device for performing cardiac ablation.

In addition to the various anatomies and body cavities for which specific devices and methods have been disclosed, it is not surprising that the devices themselves vary widely in their structures. For example, U.S. Pat. No. 5,575,788, which issued to Baker et al. for a "Thin Layer Ablation Apparatus," incorporates an expandable member in which the electrolyte is delivered to the ablation site, such as the endometrium, through the expandable member. This is quite different from the Mulier et al. device, mentioned earlier, which delivers a conductive fluid to the ablation site by injection through a hollow, helical electrode. In light of the above, it is understandable that in general, the trend with electrolyte assisted ablation has been toward the development of a specific device and a specific method for use in a specific body cavity.

Regardless which particular body cavity is involved, or what particular device is employed, there are certain factors which need to be considered when performing electrolyte assisted ablation. Specifically, the factors which will impact on the efficacy of the electrolyte assisted ablation include: the extent and nature of the surface area to be ablated; the conductivity of the electrolyte; the power requirements; time; and the temperature at which the tissue will be adequately ablated.

An ability to control any medical device during its operation is always an important consideration. This is particularly so when tissue is being ablated by the device. Accordingly, it is very desirable that, at the very least, there be some capability for "open-loop" control of the device. Preferably, the device can also be operated with "closed-loop" control.

In light of the above, it is an object of the present invention to provide a device, and a method for its use, which is effective for electrolyte assisted ablation of superficial tissue in the esophagus. It is another object of the present invention to provide a device, and a method for its use, which is capable of uniformly ablating a selected surface area of tissue. Yet another object of the present invention is to provide a device which is capable of controlling the depth of tissue ablation over a selected surface area using either open-loop or closed-loop control methods. Still another object of the present invention is to provide a device for performing electrolyte assisted ablation which is operationally simple to use, relatively easy to manufacture, and comparatively cost effective.

SUMMARY OF THE INVENTION

A device and method for the ablation of tissue from the surface of the esophagus includes a catheter, or similar type fluid delivery system, which has a distal end that is insertable into the esophagus. The catheter also has a proximal end which remains extracorporeal. More specifically, the catheter or fluid delivery system is formed with a lumen for passing a conducting medium, such as an electrolytic solution, through the catheter. The device also includes a radio frequency (r.f.) probe which can be selectively extended from the distal end of the catheter. In the preferred embodiment of the present invention, the catheter includes a barrier that can be deployed beyond the distal end of the catheter and advanced into the cardia of the stomach. When so positioned, the barrier creates an esophageal volume between the barrier and the distal end of the catheter. In the preferred embodiments of this invention, the barrier may be either an inflatable balloon or a resilient disk.

In the operation of the present invention, the distal end of the catheter is first inserted into the esophagus and positioned as desired. The balloon is then advanced from the distal end of the catheter and into the stomach. As indicated above, the balloon is then inflated to create the esophageal volume. To assist in establishing this esophageal volume, and to enhance the barrier seal, a viscous gel may be placed on the outer surface of the balloon. Next, an electrolyte, such as a saline solution, is introduced into the esophageal volume. Importantly, as the saline solution floods the esophageal volume, it submerges the r.f. probe and covers the surface area of the esophagus that is to be ablated. The r.f. probe can then be activated to ablate the metaplastic tissue that has been covered by the saline solution in the esophageal volume. Typically, the r.f. probe is activated in accordance with a regimen which results in the ablation of tissue in the esophageal volume to a depth of approximately one to two millimeters (1.0 to 2.0 mm).

Using the device of the present invention, ablation of the metaplastic tissue in the esophagus can be accomplished by either open-loop or closed-loop control procedures. Open-loop ablation may be accomplished in at least three ways. In the simplest procedure, a look-up table or algorithm is used to determine the length of time needed to ablate tissue to a certain depth, given a particular energy level. Second, anatomical measurements of the area of tissue to be ablated can be taken. Using a look-up table or algorithm, the correct energy level and/or duration of therapy can then be determined. Third, an impedance measurement of the tissue to be ablated can be taken prior to the procedure. Again, an algorithm or look-up table can then be used to determine the required energy level and/or duration of therapy. For any of these open-loop procedures, the time interval determined by the algorithm or look-up table, during which the r.f. probe is activated, is established by accounting for not only any anatomical or impedance measurements, but also the concentration of the saline solution and the power which is applied to the r.f. probe.

On the other hand, closed-loop control of the ablation procedure may be done in one of at least three ways. First, the clinician can visually monitor the tissue being ablated and stop the procedure when a particular color or texture change occurs. In the esophagus, for example, it is known that the tissue turns color from pink to white when the protein elements of the mucosal tissue denature. Second, and alternatively, the temperature of the tissue can be monitored during the procedure, and ablation ceased when a target temperature is reached. The temperature monitoring for this particular closed-loop control procedure can be done either on the surface of the tissue being ablated, or at a specified depth into the tissue, e.g., one to two millimeters (1.0–2.0 mm). Third, the impedance of the tissue can be monitored, and ablation stopped when the impedance of the tissue reaches a certain absolute or relative impedance.

In an alternate embodiment of the present invention, the catheter can include an additional balloon which is mounted on the catheter proximal to the distally advanced balloon. This additional balloon can thus be used to establish a proximal barrier which, in cooperation with the barrier established by the distally advanced balloon, will effectively define and enclose the esophageal volume wherein the metaplastic tissue is to be ablated.

In another embodiment, the device includes a porous carrier which is positioned between an optional distal barrier and the distal end of the catheter. For this embodiment, the r.f. probe can be surrounded by the porous carrier. The optional distal barrier serves to substantially prevent the electrolyte from migrating beyond the intended esophageal volume. By way of example, the distal barrier may be a balloon element, or an oversized, non6 porous sponge element, or a resilient disk. The porous carrier and the optional distal barrier (which is distal to the porous carrier) are advanced together with the catheter into the esophagus. In the case where the catheter is an endoscope, the porous carrier and distal barrier may be sized to fit through a working channel of the endoscope. In this case, the carrier and barrier may be made from compressed sponge materials that expand when wet. Alternatively, the carrier and barrier may be confined by a sleeve or shroud that is removed after they are passed through the channel of the endoscope. In all cases, advancement is continued until the distal barrier establishes a seal in the vicinity of the cardia to effectively isolate the esophagus from the stomach. At the same time, the porous carrier is placed in, at least, partial contact with the metaplastic tissue that is to be ablated. An open space can be preserved between the porous carrier and the distal end of the catheter.

Once the porous carrier is properly placed, conducting medium is delivered to the carrier. The amount of conducting medium delivered can either be pre-determined, or, if visualization of the carrier is possible, conducting medium is delivered until the carrier is clearly saturated. In the case where the conducting medium is a transparent solution, such as saline, and where visualization of the carrier is possible, it may be desirable to add an additional amount of medium into the open space between the carrier and the catheter. This can help ensure that all of the tissue that is to be ablated is covered by the conducting medium. It can also allow for visual feedback of the ablation process; for example, by stopping the ablation when the wall of the esophagus (as seen through the transparent conducting medium) changes from pink to white. In any event, once the proper volume of conducting medium has been delivered, the r.f. probe can then be activated.

For all embodiments of the present invention, either the open-loop or the closed-loop procedures mentioned above can be used.

BRIEF DESCRIPTION OF THE DRAWINGS

The novel features of this invention, as well as the invention itself, both as to its structure and its operation, will be best understood from the accompanying drawings, taken in conjunction with the accompanying description, in which similar reference characters refer to similar parts, and in which:

FIG. 6A is a schematic diagram of the device of the present invention inserted into an esophagus prior to deployment of its distal barrier;

FIG. 6B is a view of the device shown in FIG. 5A after deployment of the distal barrier;

FIG. 7 is a perspective view of another embodiment of the device for use in performing electrolyte assisted ablation in accordance with the present invention;

DESCRIPTION OF THE PREFERRED EMBODIMENT

Figure 1A:
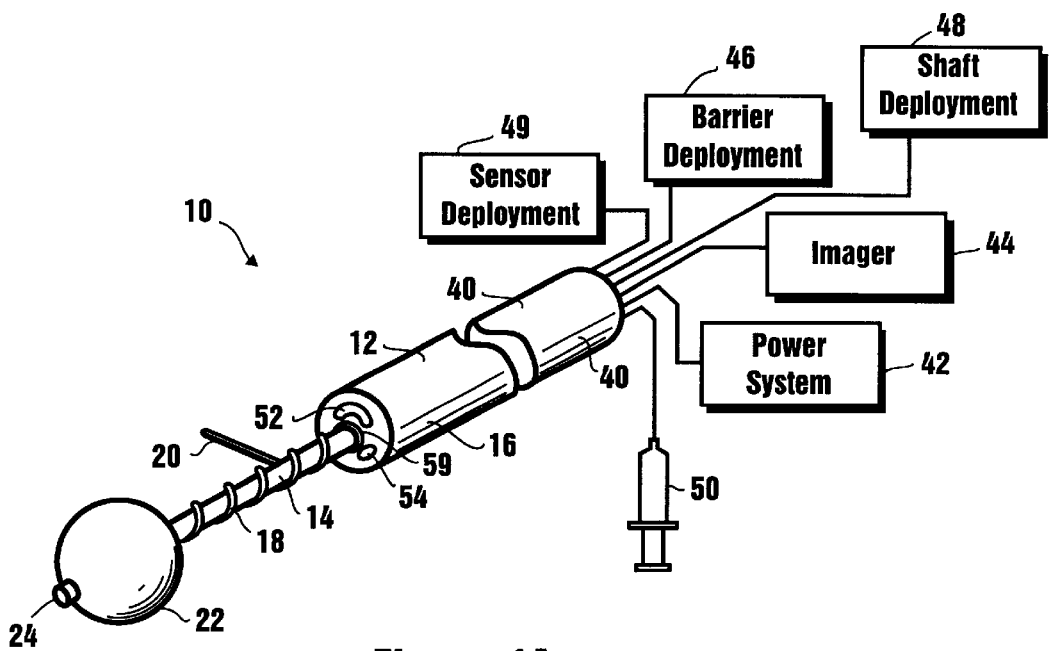
FIG. 1A is a perspective view of a device for use in performing electrolyte assisted ablation in accordance with the present invention.

Referring initially to FIG. 1A, a device for use in the electrolyte assisted ablation of tissue in accordance with the present invention is shown and generally designated 10. More specifically, as shown in FIG. 1A, the device 10 includes a multi-lumen tube, or catheter 12, and a deployable shaft 14 which can be deployed from the distal end 16 of the catheter 12. Also included are an electrode 18 and a temperature sensor probe 20 which, as shown in FIG. 1A, are supported on the deployable shaft 14. It is to be appreciated, however, that the particular configurations shown in FIG. 1A for supporting the electrode 18 and the temperature sensor probe 20 are only exemplary. The use of other structure on the device 10 for these purposes is also contemplated for the present invention. It is also shown in FIG. 1A that the device 10 incorporates a barrier 22 which is mounted on the distal end 24 of the deployable shaft 14. Although the barrier 22 shown in FIG. 1A is an inflatable balloon, which happens to be shown in its inflated state, it is contemplated that any expandable barrier 22 which is capable of establishing a seal (preferably, a fluid tight seal) across a body cavity will suffice for the present invention. For example, the barrier 22 may be expandable elements, such as an umbrella (not shown), or a gel-filled deformable sac (also not shown). Further, the barrier 22 may be a low-durometer polymer which can be shaped in-situ to establish a seal across the body cavity.

Figure 1B:
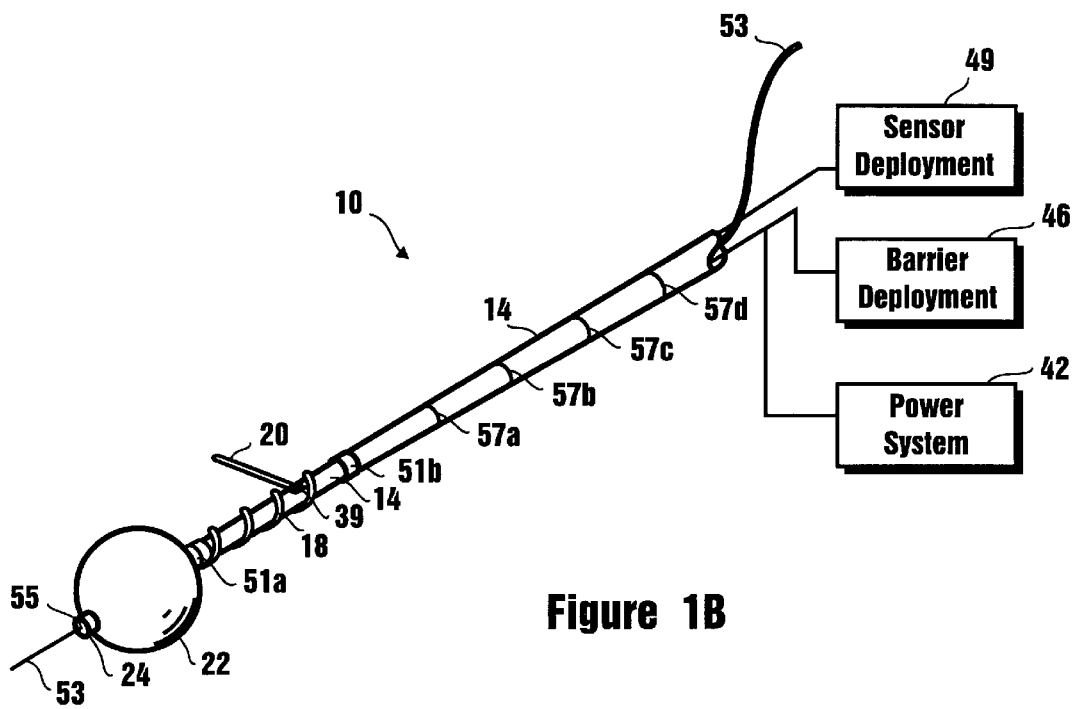
FIG. 1B is a perspective view of a basic embodiment of the device of the present invention.

In FIG. 1B an embodiment of the device 10 is shown for a basic configuration. Specifically, as intended for the present invention, the device 10 essentially includes the shaft 14 on which are mounted the barrier 22, the electrode 18 and the sensor probe 20. As will be appreciated from an understanding of the disclosure for the device 10 set forth herein, additional components can be, and usually are, used with these basic components to provide a variety of configurations for the device 10.

Figure 2A:
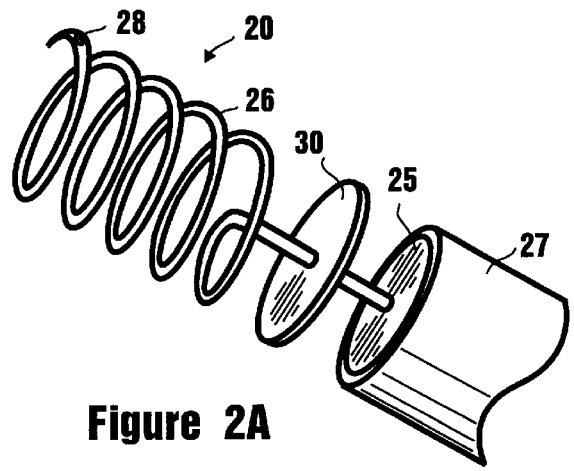
FIG. 2A is a perspective view of a sensor probe tip that is useable with the device of the present invention.
Figure 2B:
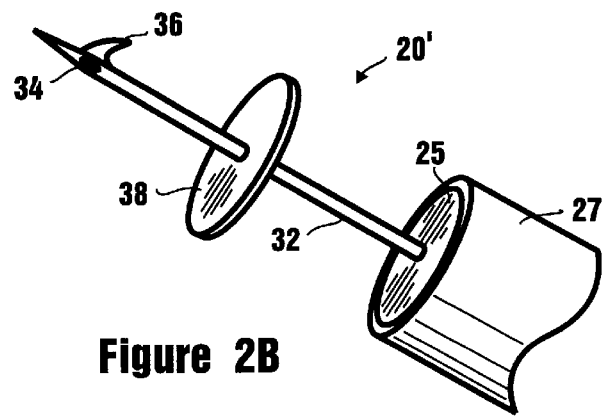
FIG. 2B is a perspective view of an alternate embodiment for the sensor probe tip.

Referring now to FIGS. 2A and 2B, it will be seen that the temperature sensor 20 can be configured with alternate embodiments. Specifically, FIG. 2A shows a temperature sensor 20 which incorporates a helical needle 26 that can be slidably extended from the distal opening 25 of the sensor guide tube 27, which may be hollow tubing such as a hypotube. A thermocouple, or thermistor, 28 is mounted on the helical needle 26 substantially as shown, and this thermocouple 28 is electrically connected to appropriate conduit, i.e. wires (not shown), which may be located inside the helical needle 26 or which may in part include the helical needle 26 itself. Further, the thermocouple 28 includes a depth stop 30 which is provided to allow helical needle 26 to be screwed into tissue, to secure and hold the thermocouple (thermistor) 28 at an accurate depth in the tissue. Preferably, this depth is in the range between one and two millimeters (1–2 mm). FIG. 2B shows an alternate embodiment for the temperature sensor 20' wherein a straight elongated needle body 32 extends from sensor guide 27. For this particular embodiment of the temperature sensor 20' a thermocouple (thermistor) 34 is mounted on the needle body 32, and a barb 36 projects from the needle body 32 substantially as shown. Similar to the engagement of the helical needle 26 into tissue, the purpose of the barb 36 is to secure and hold its thermocouple (thermistor) 34 in the tissue in order to prevent an unwanted dislodgment of the temperature sensor 20. The thermocouple (thermistor) 34 is connected to appropriate conduits, i.e. wires (not shown), which may be located inside the needle body 32 or which may in part include the needle body 32 itself. Additionally, a depth stop 38 is provided so that when the needle body 32 is penetrated into tissue, the depth to which the thermocouple (thermistor) 34 is embedded can be accurately established. It will be appreciated that the embodiment shown in FIG. 2A may also have a depth stop 38 to further control the depth of placement. In the operation of the sensors 20, it may be necessary for the sensors 20 to be retracted into a channel 39 in the shaft 14 (see FIG. 1B). If so, a suitable material for the sensor guide tube 27 would be a "superelastic" or "shape memory" material such as Nitinol.

Returning to FIG. 1A, it will be seen that various components are either connected, attached or affixed to the proximal end 40 of the catheter 12. These components will, of course, remain extracorporeal during use of the present invention and, when used, they are each operationally associated with specific structure near the distal end 16 of the catheter 12. As contemplated for the present invention, the attachable components can include a power system 42, an imager 44, a barrier deployment device 46, a shaft deployment device 48 and a fluid source 50.

With specific regard to the imager 44, it is to be understood that the imager 44 can be of any type well known in the pertinent art which is able to transfer images from one end of a catheter (tube) 12, i.e. the distal end 16, to its other end, i.e. proximal end 40. To do this for the device 10 of the present invention, a viewing lens 52, with a source of illumination, is provided at the distal end 16. In one embodiment of the device 10, the viewing lens 52 may be coupled with the imager 44 via a coherent fiber optic bundle (not shown). If so, an image that is illuminated in the spatial volume which is external and immediately adjacent the distal end 16 of the catheter 12 will be seen optically at the imager 44. Alternatively, the viewing lens 52 may be coupled with the imager 44 via a charge-coupled device (CCD) and an electrical cable (not shown). In this case, the imager 44 may include a video processor and a video monitor. In either case, the viewing lens 52 needs to include some apparatus at the distal end 16 of catheter 12 for illuminating the space to be viewed, i.e. the spatial volume which is external and immediately adjacent the distal end 16 of the catheter 12. For purposes of the present invention, this illumination apparatus can be of any type well known in the pertinent art.

It will be appreciated that visual imaging means need not be included for the ablation system disclosed herein to be operable. For example, instead of visual imaging means, a fluoroscopic imaging system may be used to guide placement of the ablation probe. Alternatively, the probe may be placed "blindly" based on knowledge of the distance from the patient's incisors (or other fixed anatomical feature) to the desired location of the probe. Such information may be obtained from an endoscopic or x-ray exam, for example. To implement these procedures, various different structures for the device 10 may be incorporated. Specifically, when fluoroscopy is to be used for placement of the device 10 in a patient, radiopaque markers 51 can be placed on the shaft 14. As suggested in FIG. 1B, the placement and location of the markers 51 on the shaft 14 can provide the operator with information about the device 10. For example, in FIG. 1B, the marker 51a is located at the distal margin of the electrode 18, while the marker 51b is located at its proximal margin. Placement of the electrode 18 can then be accomplished by well known fluoroscopic methods. Another possibility for assisting in the placement of the device 10 is with the use of a guidewire 53. For those configurations of the device 10 which are intended to function with a guidewire 53, a lumen 55 is provided in the shaft 14. With proper prior placement of the guidewire 53, an end of the guidewire 53 can be inserted into the lumen 55, and the shaft 14 of device 10 can then be advanced over the guidewire 53 in accordance with well known surgical procedures. A determination of the exact position of the shaft 14 on the guidewire 53 can be made using length demarcations 57 which are accurately positioned on the shaft 14 in a manner as substantially shown in FIG. 1B. There, the location of the length demarcations 57a–d are only exemplary. While the discussion here of the markers 51, the guidewire 53 and the length demarcations 57 has been given in the context of the configuration for device 10 shown in FIG. 1B, it is to be appreciated that these features, as well as all of the other specific features disclosed in this specification, can be selectively incorporated in other configurations of the device 10.

A fluid source 50 is provided for the device 10 and, as indicated in FIG. 1A, it is connectable in fluid communication through a lumen with a fluid port 54 at the distal end 16 of catheter 12. For purposes of the present invention, the fluid source 50 can be any device well known in the art, such as a syringe. Further, it should be noted that fluid source 50 and a lumen and fluid port 54 are not required elements of the present invention. Specifically, any means for delivering fluid to the space adjacent to barrier 22 will suffice, such as simply pouring fluid into a space alongside catheter 12.

The device 10 also includes a barrier deployment device 46 which is operationally connected with the barrier 22 for causing the barrier 22 to deploy or expand. Preferably, as shown in FIG. 1, the barrier 22 is an inflatable balloon. Therefore, the barrier deployment device is preferably a fluid pump which is connected in fluid communication with the balloon barrier 22. As intended for the present invention, the connection between the inflation means 50 and the balloon barrier 22 is via a lumen (not shown) which passes through both the catheter 12 and the shaft 14. With this connection the barrier deployment device 46 can be activated to selectively inflate the balloon barrier 22.

The shaft deployment device 48, shown in FIG. 1A, is connected directly with the shaft 14 for extending the shaft 14 through lumen 59 and from the distal end 16 of the device 10. Shaft deployment device 48 is also used for retracting the shaft 14 into the lumen 59 at the distal end 16 of the device 10. Although FIG. 1A shows the shaft 14 in its extended configuration, it is to be appreciated that by selective manipulation of the probe deployment device 48, the shaft 14 can be retracted or withdrawn into the catheter 12. As intended for the present invention, the electrode 18, the temperature sensor 20, and the barrier 22 will travel with the shaft 14 and thereby be selectively extended or retracted by the probe deployment device 48. It will be appreciated that the profile of the barrier balloon 22 in its deflated state (it is shown in its inflated state in FIG. 1A), as well as the profile of electrode 18 and sensor 20, must be dimensioned to be received into and pass through the lumen 59 during extension and retraction of the balloon 22 from the catheter 12. Alternatively, shaft 14 and its associated elements may have a fixed relationship relative to catheter 12; thus shaft deployment device 48 is optional. Similarly, sensor deployment device 49 can be used to position the temperature sensor 20. For the embodiment of the temperature sensor 20 shown in FIG. 2A, the sensor deployment device 49 is manipulable to rotate the helical needle 26, and to thereby securely embed the helical needle 26 into tissue. On the other hand, for the embodiment of the temperature sensor 20 shown in FIG. 2B, the sensor deployment device 49 is operable to drive the needle body 32 into tissue to securely embed the barb 36 in the tissue. For either embodiment, the respective depth stops 30, 38 can be used to ensure that the respective thermocouple (thermistor) 28, 34 is accurately placed.

As indicated above, there are several ways in which the device 10 can be controlled during its operation. These include both closed-loop and open-loop control. Accordingly, several different type power systems 42 can be employed. Insofar as closed-loop control is concerned, there are generally three different feedback parameters which can be monitored. These parameters are: temperature, impedance and tissue color. Closed-loop monitoring of the first parameter, i.e. temperature, requires use of the temperature sensor 20 for measuring the temperature of the tissue to be ablated. Closed-loop monitoring of the second parameter, i.e. impedance, requires use of the electrode 18 for measuring the impedance encountered by the electrode 18 during operation of the device 10. Finally, closed-loop monitoring can be accomplished using the imager 44 to determine color changes in the tissue being ablated.

Figure 3A:
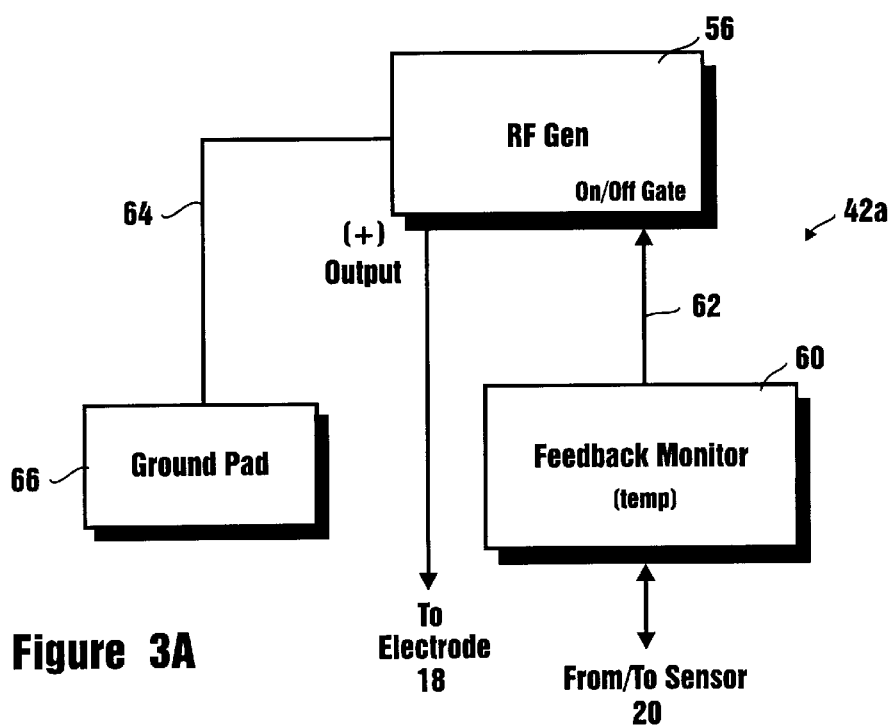
FIG. 3A is a schematic diagram of a closed-loop temperature control for the r.f. power system of the present invention.
Figure 3B:
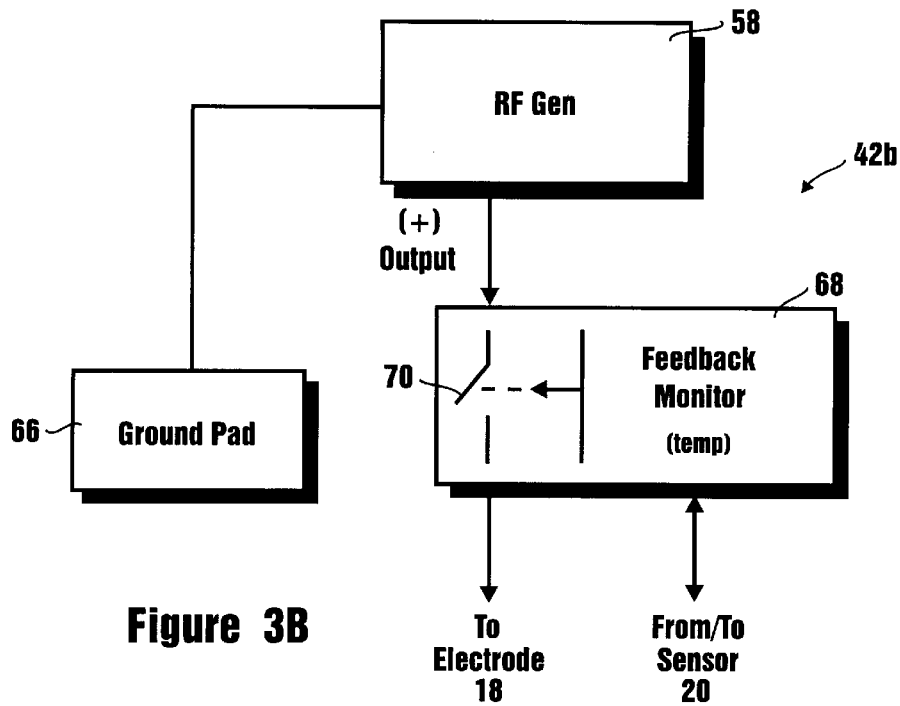
FIG. 3B is a schematic diagram of an alternative closed-loop temperature control for the r.f. power system.

FIGS. 3A and 3B, respectively, illustrate two embodiments for the power system 42 which may be used for closed-loop temperature control of the device 10. Specifically, the power system, generally designated 42a in FIG. 3A, includes an RF generator 56 which incorporates an on/off gate. In an alternative embodiment for closed-loop temperature control, a power system, generally designated 42b in FIG. 3B, includes an RF generator 58 which does not incorporate an on/off gate. Preferably, both RF generators 56, 58 are of a type well known in the pertinent art which are commercially available and which are capable of generating radio frequency energy with a power level of between approximately five and five hundred Watts (5–500 W). The only real difference between the RF generators 56, 58 is the presence or absence of an on/off gate.

For the embodiment of the power system 42a shown in FIG. 3A, a temperature feedback monitor 60 is connected by a line 62 to the on/off gate of RF generator 56. The feedback monitor 60 is also connected directly to the temperature sensor 20. Additionally, The RF generator 56 is connected via a line 64 to a ground pad 66, and it is also connected directly to the electrode 18. With these connections, the temperature of a tissue zone can be detected by the thermocouple (thermistor) 28, 34 of temperature sensor 20 and relayed to the feedback monitor 60. Whenever the monitor 60 detects a predetermined temperature for the tissue, the monitor 60 will activate the on/off gate of RF generator 56 to discontinue the transmission of r.f. energy through the electrode 18.

For the embodiment of the power system 42b shown in FIG. 3B, a temperature feedback monitor 68 is provided which includes a switch 70. The temperature sensor 20 is connected directly to the monitor 68, and the RF generator 58 is connected via the switch 70 of monitor 68 to the electrode 18. Again, a ground pad 66 is provided. With these connections, closed-loop control is established so that whenever the monitor 68 detects a predetermined temperature, the switch 70 is activated to disconnect the RF generator 58 from the electrode 18, and thereby discontinue the transmission of r.f. energy through the electrode 18.

Figure 4A:
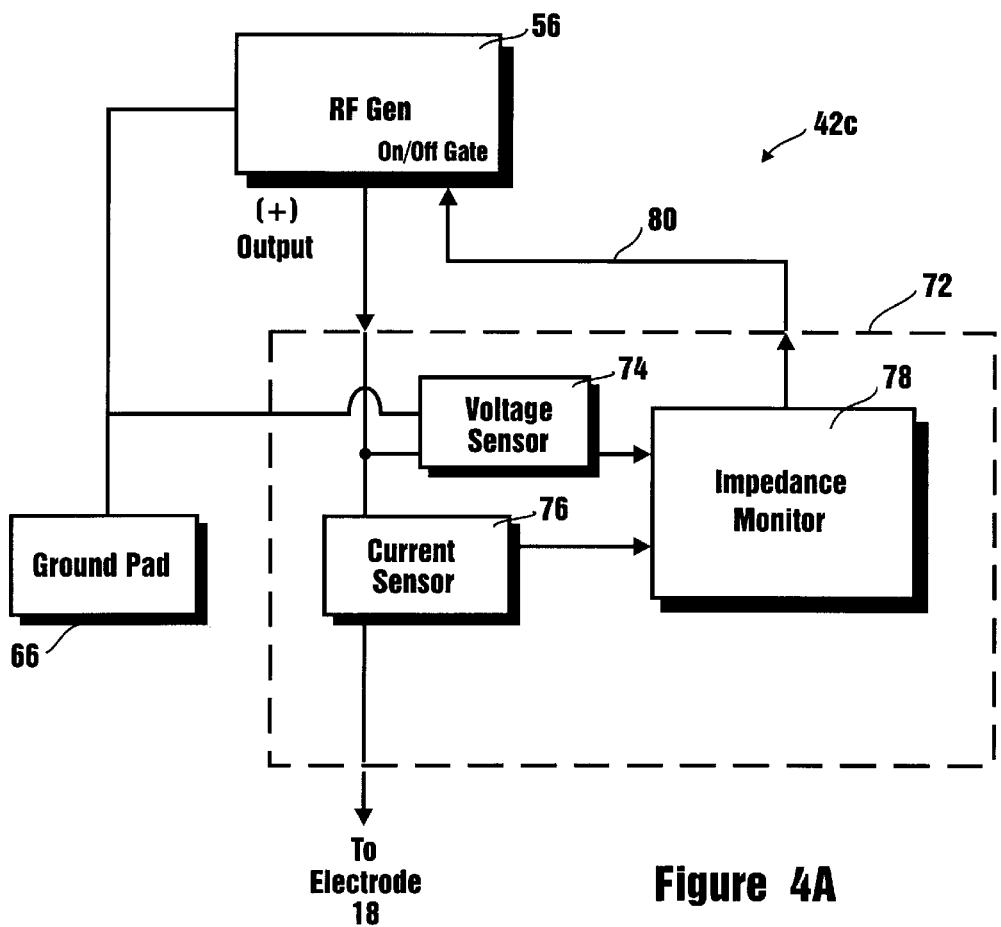
FIG. 4A is a schematic diagram of a closed-loop impedance control for the r.f. power system of the present invention.
Figure 4B:
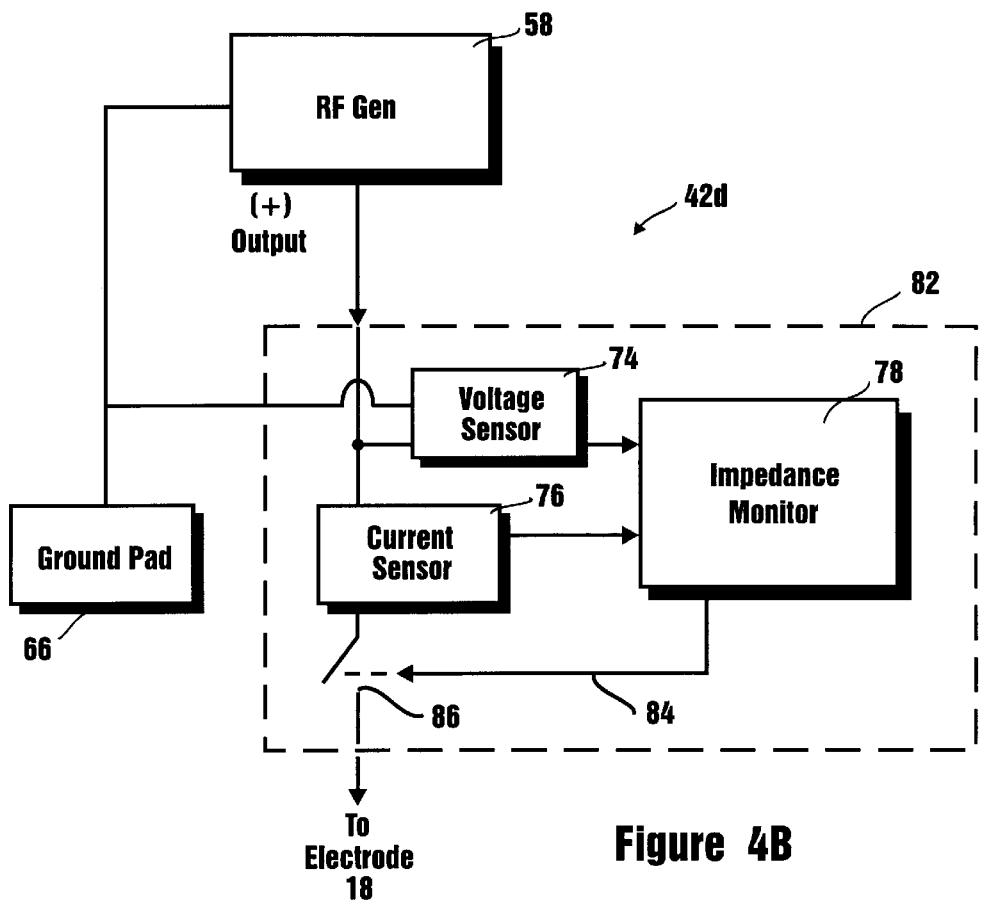
FIG. 4B is a schematic diagram of an alternative closed-loop impedance control for the r.f. power system.

FIGS. 4A and 4B respectively illustrate two embodiments for the power system 42 which may be used for closed-loop impedance control of the device 10. Specifically, the power system, generally designated 42c in FIG. 4A, includes an RF generator 56 which, like the RF generator 56 shown in FIG. 3A, incorporates an on/off gate. Similarly, a power system, generally designated 42d in FIG. 4B, includes an RF generator 58 (like the one shown in FIG. 3B) which does not incorporate an on/off gate. As before with the embodiments of power systems 42a and b, both of the RF generators 56, 58, respectively used in power systems 42c and d, are preferably of a type well known in the pertinent art which are commercially available and capable of generating radio frequency energy with a power level of between approximately five and five hundred Watts (5–500 W).

In FIG. 4A, it will be seen that a power system, generally designated 42c, has a feedback monitor 72 which includes a voltage sensor 74 and a current sensor 76. Both the voltage sensor 74 and current sensor 76 are each connected directly to an impedance monitor 78. Further, the impedance monitor 78 is connected via a line 80 to the on/off gate of the RF generator 56. Further, as shown in FIG. 1, the voltage sensor 74 is connected to the RF generator 56, to the electrode 18 through the current sensor 76, and to the ground pad 66. As so connected, the voltage sensor 74 provides a voltage input to the impedance monitor 78. The current sensor 76, meanwhile, is connected between the RF generator 56 and the electrode 18 to provide a current input to the impedance monitor 78. With these inputs, the impedance monitor 78 provides a closed-loop control for the device 10 by activating the on/off gate of RF generator 56 to discontinue the transmission of r.f. energy from the electrode 18 whenever a predetermined impedance is measured between electrode 18 and ground pad 66.

An alternate embodiment for a power system, which is generally designated 42d in FIG. 4B, is shown to include a feedback monitor 82. The difference between feedback monitor 82 of power system 42d (FIG. 4B) and the impedance monitor 78 of power system 42c (FIG. 4A) is primarily due to the absence of an on/off gate in the RF generator 58. In all other respects the two power systems 42c and d are essentially the same. Both the voltage sensor 74 and the current sensor 76 still respectively provide voltage and current inputs to the impedance monitor 78. For this embodiment, however, the impedance monitor 78 of feedback monitor 82 is connected via a line 84 to a switch 86. Thus, instead of activating an on/off switch in the RF generator 56, the impedance monitor 78 activates the switch 86 for the same purpose.

As indicated above, a third method for establishing closed-loop feed back control for the device 10 of the present invention is provided by the imager 44. For this method of control, the RF generator 56, 58 can be manipulated by the operator in response to visual cues from the imager 44. Specifically, the imager 44 can be used to visually or optically determine when ablated tissue has turned from pink to white, an indication that the protein elements of the mucosal tissue have denatured. When this color change occurs, the RF generator 56, 58 of power system 42 can be shut down to discontinue the transmission of r.f. energy through the electrode 18.

Open-loop control of the device 10 can be accomplished by first measuring either the surface area or the impedance of the tissue to be ablated. An algorithm or look-up table can then be consulted to determine the energy level and/or the time duration of energy application that is required to ablate the tissue. The electrode 18 can then be appropriately energized by an RF generator 56, 58 to provide the required energy. For the present invention, the closed-loop methods for control of the device 10 are preferred.

Figure 5A:
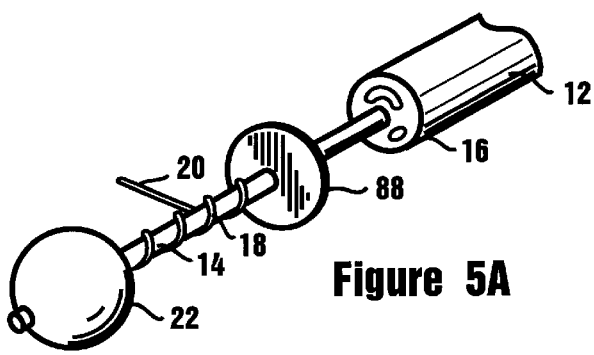
FIG. 5A is a perspective view of an alternate embodiment for the distal end of the device of the present invention.
Figure 5B:
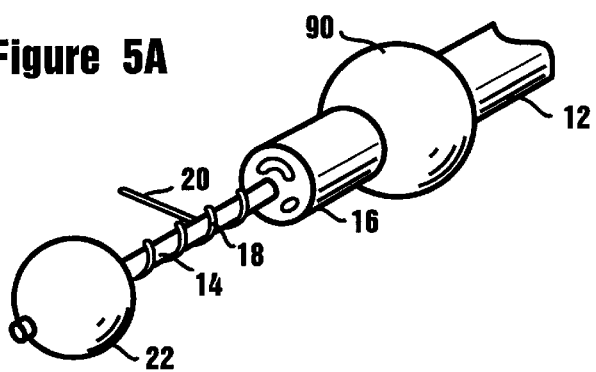
FIG. 5B is a perspective view of another alternate embodiment for the distal end of the device of the present invention.

Alternate embodiments for the catheter 12 of the present invention are shown in FIGS. 5A and 5B. Specifically, both of these alternate embodiments employ a second barrier which effectively establishes a volume space between the barrier 22 and the second, more proximal, barrier. In FIG. 5A, for example, a second barrier balloon 88 is positioned on the shaft 14 proximal to both the temperature sensor 20 and the electrode 18, but distal to the distal end 16 of catheter 12. For this particular embodiment, it may be necessary for the second barrier balloon to be transparent so that imager 44 may be used. As shown in FIG. 5B for another alternate embodiment of the catheter 12, a second barrier balloon 90 can be located proximal to the distal end 16 of the tube catheter 12, substantially as shown. For both of the embodiments shown in FIGS. 5A and 5B the barrier deployment device 46 will then need to also be placed in fluid communication with the second barrier 88, 90 so that operation of the device 46 can selectively inflate either, or both, the barrier balloon 22 and the second barrier balloon 88, 90. With the use of a second barrier 88, 90 it is particularly important to be careful not to obstruct the distal end 16 of catheter 12 and thereby prevent any beneficial use of the imager 44.

In another embodiment for the present invention, a device 106 is provided which includes many of the same features disclosed above for the device 10. For this reason, where there are similarities in structure, the device 10 and the device 106 use the same nomenclature and numerical designators. As shown in FIG. 7, unlike the device 10, the device 106 may not employ a barrier balloon 22. Instead, the device 106 has a shaft 14 that extends from its distal end 16 on which a porous carrier 108 is mounted. Further, there is a disk-like barrier 110 which is also mounted on the shaft 14, and located adjacent and distal to the porous carrier 108. For purposes of the present invention, it is preferable for the porous carrier 108 to be made of an open cell sponge-like material of a type well known in the pertinent art. Importantly, whatever material is used for the porous carrier 108, it must be capable of becoming effectively saturated with the particular conducting medium 102 (See FIG. 8A) that is being used. On the other hand, it is preferable for the disk-like barrier 110 to be made of a closed cell foam material which does not absorb fluids. Alternatively to the closed cell foam, the barrier 110 can be made of any suitably resilient material which will comply with the anatomy of the esophagus 92 and establish a seal in the vicinity of the cardia at the base of the esophagus 92. As will be appreciated by the skilled artisan, whatever material is used for the porous carrier 108, and possibly the disk 110, may need to satisfy specific dimensional requirements. Specifically, for the embodiment of the device 10 which incorporates a catheter 12, the material should be compressible in order to permit extension and retraction of the carrier 108 into the lumen 59 of catheter 12. For this purpose, a compressible foam that slowly recovers after being compressed may be used, such as an E-A-R foam made by Aearo Corporation, Boston, Mass. Alternatively, for embodiments of the device 10 which do not incorporate a catheter, such as the configuration for device 10 shown in FIG. 1B, a sleeve (not shown) can be positioned over the porous carrier 108 and disk 110 during insertion of the device 10 into a patient. Once the porous carrier 108 has been properly placed in the esophagus 92 of the patient, the sleeve can be removed to allow the porous carrier 108 and disk 110 to assume their unconstrained shapes.

Figure 8A:
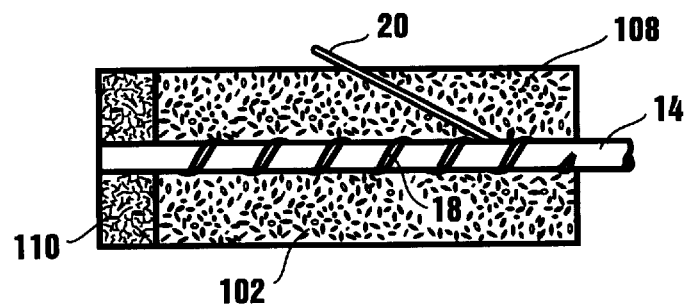
FIG. 8A is a cross sectional view of a portion of the device as seen along the line 8—8 in FIG. 7.

As perhaps best seen with reference to FIG. 8A, the device 106, like the device 10, incorporates an electrode 18 and a sensor 20, and uses them for similar purposes. For the device 106, however, both the electrode 18 and the sensor 20 are embedded inside the porous carrier 108 substantially as shown in the FIG. 8A. Further, it is to be appreciated that for this version of the present invention, the porous carrier 108 is filled, saturated or impregnated with the conducting medium 102.

Figure 8B:
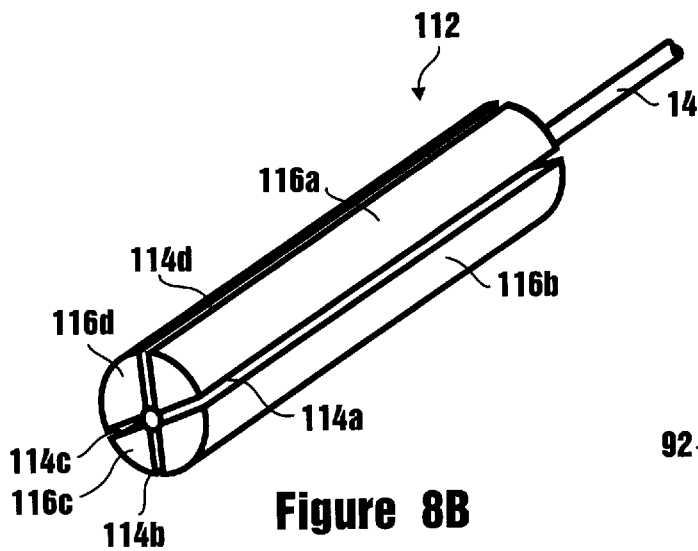
FIG. 8B is a perspective view of an alternate embodiment of the sponge for the device shown in FIG. 7.

It is recognized that it may be desirable to ablate only certain circumferential regions of the metaplastic region in the esophagus 92 because it is suspected that a deep, full circumferential ablation may lead to the formation of a stricture after the ablative procedure. For such circumstances, the alternative embodiment for a porous carrier 112 as shown in FIG. 8B can be used. As shown for the porous carrier 112, a plurality of partitions 114, of which the partitions 114*a–d* are exemplary, can be used to divide the carrier 112 into radially arranged segments or quadrants 116, of which the segments 116*a–d* are exemplary. For the embodiment of the porous carrier 112, it may be preferred to make the segments 116 of an open cell sponge-like foam, such as suggested above for the porous carrier 108. At the same time, it may be preferred to make the partitions 114 of a closed cell foam, such as suggested above for the disk 110. Accordingly, the conducting medium 102 can be exclusively and selectively directed to one, or more, segments 116 to satisfy the particular ablation profile that is desired.

OPERATION

In the operation of the device 10 of the present invention, the catheter 12 is inserted into the esophagus 92 of a patient. The catheter 12 is then advanced to a location substantially as shown in FIG. 6A. Specifically, the distal end 16 of the catheter 12 is positioned in the esophagus 92 at a proximal distance from the stomach 94 so that the esophageal tissue 96 which is to be ablated is positioned between the distal end 16 of the catheter 12 and the cardia 98 of the stomach 94. With the catheter 12 so positioned, the barrier 22 can be deployed as shown in FIG. 6B. Specifically, for deployment of the barrier 22 from the catheter 12, the barrier deployment device 46 is used to advance a deflated balloon (barrier 22) on the shaft 14 past the cardia 98. The barrier (balloon) 22 is then expanded (inflated) using the device 46 to thereby seal the cardia 98 and isolate the esophagus 92 from the stomach 94. To assist and enhance the sealing action of the barrier 22, upward traction may be applied to the barrier 22 by pulling on the shaft 14. Additionally, the surface area of the barrier 22 may be covered with a viscous gel or some other appropriate sealing substance that is well known and used in the pertinent art for this purpose.

In addition to the deployment of the barrier 22 from the catheter 12, the temperature sensor 20 is also deployed from the catheter 12 by using the sensor deployment device 49. Specifically, the temperature sensor 20 is deployed and moved into contact with the tissue 96 so as to contact or penetrate the tissue 96 to a predetermined depth (e.g. one to two millimeters). The method for deploying the temperature sensor 20 will be determined by its particular configuration and may be substantially accomplished as disclosed above.

Once the barrier 22 has been properly deployed and has effectively sealed the esophagus 92 from the stomach 94, the fluid source 50 can be activated to partially flood the esophageal volume 100 (see FIG. 6B) from fluid port 54 with a conducting medium (electrolyte) 102. Preferably, the conducting medium 102 is either a solution or a gel which contains saline. For purposes of the present invention, the esophageal volume 100 is defined as the volume inside the esophagus 92 which is bounded by the barrier 22 at its lower end, by the distal end of the catheter 12 at its upper end, and by the wall of the esophagus 92 which is located therebetween and which includes the tissue 96 that is to be ablated. Importantly, within the esophageal volume 100, the conducting medium 102 needs to be in intimate contact with all of the surface area of the tissue 96 that is to be ablated. It is also important for procedures wherein visual viewing of the ablation process is desired that there be a space 104 within the esophageal volume 100 which separates the distal end 16 of catheter 12 from the conducting medium 102.

Figure 9:
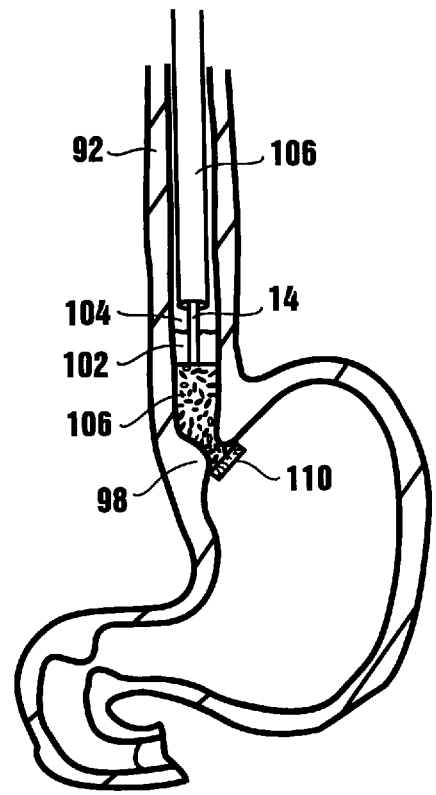
FIG. 9 is a schematic diagram of an embodiment of the present invention that has been inserted into an esophagus and advanced to position a porous carrier, filled with a conducting medium, in contact with metaplastic tissue that is to be ablated.

In the operation of the device 106 shown in FIG. 7, the porous carrier 108 may first be saturated or filled with the conducting medium 102. Alternatively, the porous carrier 108 may be left devoid of conducting medium 102 prior to insertion of the catheter 12 into the esophagus 92. In either case, the catheter 12 is inserted into the esophagus 92 to position the carrier 108 in the vicinity of the tissue that is to be ablated. As shown in FIG. 9, this also positions the barrier 110 in the cardia 98 to effectively isolate the stomach 94 from the esophagus 92. If desired, or if not done previously, additional conducting medium 102 can be introduced at this time using fluid source 50. This will effectively ensure that the carrier 108 is fully saturated, and it may also cause the deposit of additional conducting medium 102 between the carrier 108 and the distal end 16 of the catheter 12. In FIG. 9, it is to be noted that an open space 104 may be provided above the fluid level of the conducting medium 102 so that a viewing of the ablation process is possible.

As intended for the present invention, aspects of the balloon version (see FIG. 1) can be incorporated into the porous carrier version (see FIG. 7), and vice versa. For example, although not shown with this specific combination of elements, a balloon barrier 90 can be located proximal to the distal end 16 of the catheter 12 and thereby employed with the porous carrier version. For such a combination the balloon barrier 90 and the disk-like barrier 110 will act in concert to confine the conducting fluid 102 therebetween.

It is important to the operation of the present invention that the amount of tissue 96 being ablated is accurately measured. Specifically, it is normally preferable that the tissue 96 be ablated only to a depth somewhere between one and two millimeters or, perhaps more accurately, to the depth of the inner margin of the muscularis mucosae in the esophagus 92. To accurately control this ablation there is a need for some form of monitoring. Such monitoring requires there be some parameter which can be predictably and continuously measured in some way during the ablation process. As previously disclosed, it happens that the color, temperature and impedance of the tissue 96 are each effective parameters which can be monitored for this purpose. For the present invention, these parameters lend themselves to both open-loop and closed-loop control systems. In either case, regardless of the particular control mode that is to be used, the modality of the application of r.f. energy is monopolar. This requires the patient be appropriately connected with a ground, such as the ground pad 66 disclosed above with reference to FIGS. 3A, 3B, 4A and 4B.

For open-loop control of the electrolyte assisted ablation techniques of the present invention, the radio frequency power requirements and the time duration for the application of this power are obtained from appropriate algorithms or look-up tables. Specifically, one way to establish open-loop control for the ablation process is to determine the extent of the surface area of tissue 96 that is to be ablated. This can be obtained using anatomical measurements of the esophageal volume 100 that will be involved, or by measuring the amount of conducting medium 102 needed to fill the desired portion of the esophageal volume 100. Then, using empirical data for the ablation response of the tissue 96 to be ablated, the device 10 can be activated at a particular power level for a specified time duration to ablate the tissue 96. Another way to establish open-loop control for the device 10 is to measure the initial impedance of the tissue 96. Then, again using empirical data for the ablation response of the tissue 96, the power level and time duration for the ablation process can be determined from an algorithm or a look-up table. It is to be appreciated that the algorithms and look-up tables referenced here for use in the open-loop control of the device can be preprogrammed.

Closed-loop control for the methods of the present invention involve the monitoring of specific parameters of the tissue 96. In one control mode, the color of the tissue 96 is monitored during the ablation process. This is most likely done visually. Specifically, using the imager 44, the operator visually monitors the tissue 96 through the viewing lens 52 as it is being ablated. It is known that as the protein elements of the mucosal tissue denature during such an ablation that the tissue 96 will exhibit a discernible change in color from pink to white. Once this color change has been observed, the operator can consider the procedure completed, and then deactivate or stop the r.f. power system 42 from passing additional energy through the conducting medium 102.

Automatic closed-loop control for the methods of the present invention can also be used. For example, target values for the temperature or impedance of the tissue 96 can be predetermined. Then, with the sensor 20 properly positioned relative to the tissue 96 to monitor temperature, or with the electrode set to monitor impedance, the r.f. power system 42 can be activated. By controlling the r.f. energy generated by power system 42, while monitoring the temperature/impedance parameters of the tissue 96, the device 10 is able to use the preset target values for control of the ablation process. For the specific closed-loop control system wherein the impedance of tissue 96 is to be measured, it is to be understood that the impedance is measured by monitoring the voltage and the current which are actually traveling through the circuit that includes the electrode 18, any wires connected with the electrode 18, the conducting medium 102, the tissues 96, ground pad 66, and any wires connected with ground pad 66.

During, or after, any of the methods disclosed herein for the present invention, an anesthetic agent such as lidocaine may be dispensed into the volume 100 to help make the procedure more comfortable for the patient. As intended for the present invention this agent may either be actively or passively applied to the tissue 96. Active application may involve iontophoretic transfer of the agent into the tissue 96. This can be done using a direct current, which may be applied using the electrode 18 and ground pad 66. Also, upon completion of any of the methods disclosed herein, an agent may be applied to the ablated tissues 96 to improve healing or to reduce the chance of stricture formation. For example, an antibiotic agent may be applied or an anti-inflammatory agent may be applied. Like the anesthetic agent, the healing agent may be applied either passively or actively.

While the particular electrolyte assisted ablation device and methods as herein shown and disclosed in detail is fully capable of obtaining the objects and providing the advantages herein before stated, it is to be understood that it is merely illustrative of the presently preferred embodiments of the invention and that no limitations are intended to the details of construction or design herein shown other than as described in the appended claims.

What is claimed is:

1. A device for ablating selected tissue of a body cavity which comprises:
   a shaft;
   a barrier mounted on said shaft for creating a volume in the body cavity, said volume being at least partially bounded by said barrier and the selected tissue of the body cavity;
   a conductive medium introduced into a portion of said volume to contact the selected tissue;
   an electrode submersible in said conductive medium;

a radio frequency generator connected to said electrode for applying radio frequency energy through said conductive medium to ablate the selected tissue; and a porous carrier mounted on said shaft and wherein said carrier is filled with said conductive medium, and wherein said barrier is mounted on said shaft distal to said carrier to substantially prevent a flow of conducting medium from said volume distally to said barrier.

2. A device as recited in claim 1 wherein said conductive medium is an electrolytic solution containing saline.

3. A device as recited in claim 1 wherein said conductive medium is a gel.

4. A device as recited in claim 1 further comprising:

means for monitoring ablation of the selected tissue; and means for stopping the application of said radio frequency when a predetermined amount of the selected tissue has been ablated.

5. A device as recited in claim 4 wherein said monitoring means includes an impedance measurement means.

6. A device as recited in claim 4 wherein said monitoring means comprises:

illuminating means for illuminating the selected tissue bounding the volume in the body cavity; and imaging means for viewing the illuminated tissue in the body cavity.

7. A device as recited in claim 4 wherein said monitoring means includes at least one temperature probe for contact with the selected tissue.

8. A device as recited in claim 7 further comprising a depth stop mounted on said probe for deploying said temperature probe into the selected tissue to a pre-determined depth.

9. A device as recited in claim 8 further comprising a barb attached to said probe for securely holding said probe in the selected tissue.

10. A device as recited in claim 7 wherein said probe is helical shaped for screwing said probe into the selected tissue to securely hold said probe in the selected tissue.

11. A device as recited in claim 1 wherein said barrier is an inflatable balloon.

12. A device as recited in claim 1 wherein said barrier is a first barrier and said device further comprises a second barrier, wherein said second barrier is distanced from said first barrier to establish said volume therebetween.

13. A device as recited in claim 1 further comprising a porous carrier mounted on said shaft and wherein said carrier is filled with said conductive medium.

14. A device as recited in claim 1 wherein said porous carrier is made of an open cell sponge-like material.

15. A device as recited in claim 1 further comprising a grounding means for receipt of said radio frequency energy after said radio frequency energy passes through said conductive medium and said selected tissue.

16. A method as recited in claim 1 further comprising the steps of:

monitoring ablation of the selected tissue; and stopping said radio frequency energy when a predetermined amount of the selected tissue has been ablated.

17. A method as recited in claim 16 wherein said monitoring step further comprises the steps of:

illuminating the selected tissue bounding the volume in the body cavity; and imaging the illuminated tissue in the body cavity.

18. A method as recited in claim 16 wherein said monitoring step further comprises the steps of:

inserting at least one temperature probe into the selected tissue; and determining when the temperature of the selected tissue indicates a predetermined amount of the selected tissue has been ablated for initiation of said stopping step.

19. A method as recited in claim 16 wherein said monitoring step is accomplished by measuring impedance of the selected tissue.

20. A method for ablating selected tissue of a body cavity which comprises the steps of:

using a barrier mounted on a shaft for creating a volume in the body cavity, said volume being at least partially bounded by said barrier and the selected tissue of the body cavity, and wherein a porous carrier is mounted on said shaft with said barrier mounted on said shaft distal to said carrier;

introducing a conductive medium into said volume to fill said porous carrier with said conductive medium and contact the selected tissue with said conductive medium, said barrier substantially preventing the flow of said conducting medium from said volume distally to said barrier;

submersing an electrode in said conductive medium; and sending radio frequency energy through said conductive medium to ablate the selected tissue.

21. A device for ablating selected tissue of a body cavity which comprises:

a shaft;

a barrier mounted on said shaft for creating a volume in the body cavity, said barrier being a flexible resilient disk, said volume being at least partially bounded by said barrier and the selected tissue of the body cavity;

a conductive medium introduced into a portion of said volume to contact the selected tissue;

an electrode submersible in said conductive medium;

a radio frequency generator connected to said electrode for applying radio frequency energy through said conductive medium to ablate the selected tissue.

22. A device for ablating selected tissue of a body cavity which comprises:

a shaft;

a barrier mounted on said shaft for creating a volume in the body cavity, said barrier is made of a closed cell sponge-like material, said volume being at least partially bounded by said barrier and the selected tissue of the body cavity;

a conductive medium introduced into a portion of said volume to contact the selected tissue;

an electrode submersible in said conductive medium; and a radio frequency generator connected to said electrode for applying radio frequency energy through said conductive medium to ablate the selected tissue.

* * * * *